United States Patent [19]

Garces et al.

[11] Patent Number: 5,414,173
[45] Date of Patent: May 9, 1995

[54] PROCESS OF PREPARING CYCLOPENTADIENE AND SUBSTITUTED DERIVATIVES THEREOF

[75] Inventors: Juan M. Garces; Guo-shuh J. Lee; David R. Wilson, all of Midland, Mich.

[73] Assignee: The Dow Chemical Company, Midland, Mich.

[21] Appl. No.: 173,533

[22] Filed: Dec. 22, 1993

[51] Int. Cl.$^6$ ................................................ C07C 1/24
[52] U.S. Cl. ...................... 585/357; 585/350; 585/360; 585/638
[58] Field of Search ............... 585/350, 357, 359, 638, 585/639, 640, 360

[56] References Cited

U.S. PATENT DOCUMENTS

| | | | |
|---|---|---|---|
| 1,841,055 | 1/1932 | Reppe et al. | 585/611 |
| 1,923,569 | 8/1933 | Mueller-Cunradi et al. | 585/611 |
| 2,197,956 | 4/1940 | Vaughn | 260/678 |
| 2,204,157 | 6/1940 | Semon | 23/236 |
| 2,299,844 | 10/1942 | Ocon | 44/54 |
| 2,715,649 | 8/1955 | Hammond | 260/681 |
| 3,167,595 | 1/1965 | Heywood et al. | 585/357 |
| 3,595,929 | 7/1971 | Lakodey et al. | 260/666 |
| 4,423,270 | 12/1983 | Pearson | 585/639 |
| 4,499,327 | 2/1985 | Kaiser | 585/640 |
| 4,524,234 | 6/1985 | Kaiser | 585/638 |
| 4,677,242 | 6/1987 | Kaiser | 585/638 |
| 4,677,243 | 6/1987 | Kaiser | 585/638 |
| 4,873,390 | 10/1989 | Lewis et al. | 585/638 |

FOREIGN PATENT DOCUMENTS 0277003  1/1988  European Pat. Off.

OTHER PUBLICATIONS

*Organometallics*, 1987, 6, 1947–1954.
*Inorganic Syntheses*, 29, 193–197 (date unknown).
*Organometallic Syntheses*, 3, Elsevier, 1986, 489–491.
Derwent CA:87–278461/40 (1987).
Derwent CA:82497 D/45 (1980).
Derwent CA:01994 K/01 (1982).
Derwent CA:73973A/41.
Derwent CA:14623 E/08.

*Primary Examiner*—P. Achutamurthy

[57] ABSTRACT

A process of preparing cyclopentadiene or substituted cyclopentadienes, such as tetramethylcyclopentadiene. The process involves contacting under reaction conditions cyclopentenol or a substituted cyclopentenol with a catalyst selected from (1) crystalline and amorphous aluminum phosphates, (2) aluminophosphate molecular sieves, and (3) silicoaluminophosphate molecular sieves. The process produces cyclopentadienes in high isolated yields.

20 Claims, No Drawings

PROCESS OF PREPARING CYCLOPENTADIENE AND SUBSTITUTED DERIVATIVES THEREOF

BACKGROUND OF THE INVENTION

This invention relates to a process for preparing cyclopentadiene and substituted cyclopentadienes, such as tetramethylcyclopentadiene.

Cyclopentadiene is useful as a monomer and comonomer in the manufacture of polycyclopentadiene and $C_5$ hydrocarbon resins which are useful in printing inks and adhesives. Substituted cyclopentadienes, particularly tetramethylcyclopentadiene, are useful as ligands in the preparation of homogeneous single site catalysts, which are used in the production of polyolefins, notably linear low density polyethylene. For example, European Patent application publication number 0,277,003 discloses the use of bis(hydrocarbyl-substituted cyclopentadienyl) complexes of zirconium in preparing catalysts for the polymerization of ethylene.

Cyclopentadiene and methylcyclopentadiene can be obtained in small quantities from the $C_5$ fractions of naphtha crackers, or alternatively, from pyrolysis gasolines. Other substituted cyclopentadienes are more difficult to obtain. For example, the synthesis of tetramethylcyclopentadiene typically begins with the condensation of one mole of diethyl ketone with two moles of acetaldehyde to yield 2,3,5,6-tetrahydro-2,3,5,6-tetramethyl-γ-pyrone, which can be converted under acid treatment to 2,3,4,5-tetramethylcyclopent-2-enone. See for example, *InorganicSyntheses*, 29, 193, or R. B. King and J. J. Eisch, *OrganometallicSyntheses*, 3 (Elsevier, 1986), 489. The ketone can be reduced with a reducing agent, such as lithium aluminum hydride, to the corresponding 2,3,4,5-tetramethylcyclopent-2-enol. Dehydration of the tetramethyl-substituted cyclopentenol with aqueous sulfuric or hydrochloric acid yields tetramethylcyclopentadiene. Disadvantageously, the dehydration produces as by-products bis(tetramethylcyclopentenyl) ethers and polymeric cyclopentadienes. In addition, the acid must be reclaimed, or alternatively, must be neutralized creating a waste salt stream.

In view of the above, it would be advantageous to have an efficient method of dehydrating substituted cyclopentenols to substituted cyclopentadienes in high yield. It would be more advantageous if the process did not employ a liquid acid which must be reclaimed or neutralized.

SUMMARY OF THE INVENTION

This invention is a process of preparing cyclopentadiene and substituted cyclopentadienes. The process comprises contacting cyclopentenol or a substituted derivative of cyclopentenol with a catalytic amount of a catalyst under reaction conditions such that cyclopentadiene or a substituted derivative thereof is formed. The catalyst is selected from the group consisting of (1) crystalline and amorphous aluminum phosphates, (2) aluminophosphate molecular sieves, and (3) silicoaluminophosphate molecular sieves.

Advantageously, the process of this invention achieves a high yield of cyclopentadiene or substituted cyclopentadienes from cyclopentenol or substituted cyclopentenols. Minimal formation of ether by-products and polymeric cyclopentadienes occurs. More advantageously, the solid acid catalysts employed in the process of this invention are easily separated from the product stream. Accordingly, the process of this invention does not require the reclamation or neutralization of an acid and does not create a waste salt stream.

DETAILED DESCRIPTION OF THE INVENTION

In the process of this invention cyclopentenol is dehydrated in the presence of a catalyst to form cyclopentadiene. Alternatively, a substituted cyclopentenol can be dehydrated to form a substituted cyclopentadiene. Dehydration catalysts suitable for the process include crystalline and amorphous aluminum phosphates, aluminophosphate molecular sieves, and silicoaluminophosphate molecular sieves. In a preferred embodiment of this invention, tetramethylcyclopentenol is dehydrated to form tetramethylcyclopentadiene.

The cyclopentenol comprises a five-membered carbocycle wherein one of the carbons, conveniently labeled the "1" carbon, is substituted with a hydroxyl moiety and wherein two carbon atoms adjacent to each other, but excluding the "1" carbon, are unsaturated and joined by a double bond. The unsaturated double bond is preferably located between the "2" and "3" carbons or, alternatively, between the "4" and "5" carbons. In the special case where the "2" and "5" carbons are substituted with identical substituents and the "3" and "4" carbons are substituted with identical substituents, the compound having unsaturation between the "4" and "5" carbons is equivalent structurally to the compound having unsaturation between the "2" and "3" carbons. Aside from the two unsaturated carbon atoms in the five-membered ring, all of the other carbons in the ring are saturated. Any of the carbons can be substituted with one inert moiety, that is, a moiety non-reactive in the process of this invention. Preferred cyclopentenols are represented by the following isomeric formulas:

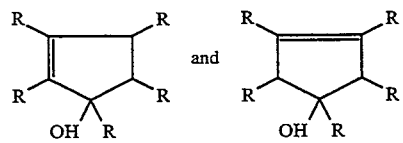

wherein each R can independently be hydrogen; a $C_{1-10}$ hydrocarbyl moiety, for example, phenyl, benzyl, or alkyl, such as, methyl, ethyl, and propyl; halogen, such as chlorine and bromine; or a ketone, amine, ether, carboxylic acid, or ester moiety. Typically, the ketone, amine, ether, carboxylic acid, or ester moiety contains at most about six carbon atoms. Moreover, whereas up to five ring carbon atoms can be functionalized with hydrocarbyl moieties, in contrast, typically at most two ring carbon atoms can be functionalized with the halogen, ketone, amine, ether, carboxylic acid, or ester moieties. More preferably, each R is independently hydrogen or a $C_{1-6}$ hydrocarbyl moiety. Most preferably, each R is independently hydrogen or methyl.

Alternatively, the R moieties on two adjacent carbon atoms can together form a saturated or unsaturated $C_{3-6}$ hydrocarbyl moiety, thereby fusing the cyclopentenol to a second ring system, as illustrated, for example, by the preferred formulas:

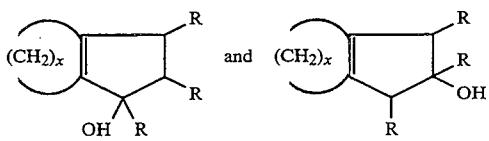

as well as the preferred formula:

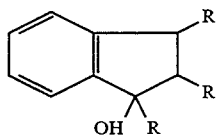

wherein R is as defined hereinabove and x is an integer ranging from 3 to 6, and is preferably 4.

As a further alternative, the cyclopentenol ring system can be fused to two saturated ring systems, or one saturated and one unsaturated ring system, as illustrated, for example, by the following preferred formula:

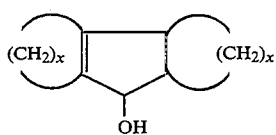

and by the preferred formula:

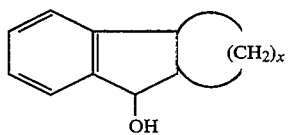

wherein x is as defined hereinabove.

Any cyclopentenol meeting the aforementioned general criteria is suitable for the process of this invention. Non-limiting examples of suitable cyclopentenols include 2-cyclopenten-1-ol, 3-cyclopenten-1-ol, 2,3,4,5-tetramethylcyclo-2-penten-1-ol, 2,3,4,5-tetramethylcyclo-3-penten-1-ol, 3,4-dimethylcyclo-2-penten-1-ol, 3,4-dimethylcyclo-3-penten-1-ol, 2-ethylcyclo-2-penten-1-ol, 3-acetoxycyclo-2-penten-1-ol, 4-methoxycyclo-2-penten-1-ol, 1-phenylcyclo-2-penten-1-ol, 1-indanol, 4,5,6,7-tetrahydro-1-indanol, 4,5,6,7-tetrahydro-2-indanol, 1,2,3,4-tetrahydro-9-hydroxyfluorene, 3-t-butylcyclo-2-penten-1ol, 1-benzyl-2,3,4,5-tetramethylcyclo-2-penten-1-ol, and 1,2,3,4,5,6,7,8-octahydro-9-hydroxyfluorene. Preferred compounds include 2,3,4,5-tetramethylcyclo-2-penten-1-ol, 2,3,4,5-tetramethylcyclo-3-penten-1-ol, 1indanol, 4,5,6,7-tetrahydro-1-indanol, and 4,5,6,7-tetrahydro-2-indanol. More preferred are 2,3,4,5-tetramethylcyclo-2-penten-1-ol and 2,3,4,5-tetramethyl-cyclo-3-penten-1-ol.

Some of the cyclopentenols described hereinabove are available commercially. Others may have to be synthesized, but methods for their synthesis are known to those skilled in the art of organic chemistry. For example, the preparation of tetramethylcyclopentenol begins, as noted hereinbefore, with the condensation of one mole of diethyl ketone with two moles of acetaldehyde to yield 2,3,5,6-tetrahydro-2,3,5,6-tetramethyl-γ-pyrone, which can be converted under acid treatment to 2,3,4,5-tetramethylcyclopent-2-enone. Details of these reactions are given in *Inorganic Syntheses*, op. cit., and *OrganometallicSyntheses*, op. cit., incorporated herein by reference.

The tetramethylcyclopentenone can be reduced with a reducing agent, such as lithium aluminum hydride, to the corresponding tetramethylcyclopentenol. Typically, for example, the reduction is effected by adding an ether solution containing the cyclopentenone to a slurry or solution of lithium aluminum hydride in ether or tetrahydrofuran. Usually, the molar ratio of ketone to lithium aluminum hydride ranges from about 1:1 to about 4:1. The addition is typically conducted at a temperature of about −78° C. The cyclopentenol can be isolated by adding to the reaction mixture, per gram of lithium aluminum hydride, about 1 ml of water, then about 1 ml of 15 percent sodium hydroxide solution, and then additionally about 3 ml of water. Thereafter, a granular solid comprising lithium aluminum salts is filtered off, and the tetramethylcyclopentenol is isolated from the filtrate by distillation or extraction. For further details see *Organometallics*, 6 (1987), 1947–1954, incorporated herein by reference.

One skilled in the art will appreciate that the aforementioned preparation of tetramethylcyclopentenol may be generalized to other tetraalkylcyclopentenols. For example, 4-heptanone and proprionaldehyde can be used to prepare 2,3,5,6-tetrahydro-2,3,5,6-tetraethyl-γ-pyrone, which can be converted under acid treatment to 2,3,4,5-tetraethylcyclopent-2-enone. The latter can be reduced, as noted hereinabove, to form 2,3,4,5-tetraethylcyclopent-2-en-1-ol.

If a penta-substituted cyclopentenol is desired, the tetrahydrotetraalkyl-γ-pyrones are prepared and then treated with alkyl or aryl lithium or a Grignard reagent to yield the penta-substituted cyclopentenol. Details of the treatment with alkyl or aryl lithium are also found in *InorganicSyntheses*, op. cit. and *OrganometallicSyntheses*, 3, op. cit..

The catalyst employed in the process of this invention comprises compounds containing aluminum, phosphorous, and oxygen. For example, the catalyst can be a crystalline or an amorphous form of aluminum phosphate, suitable examples of which include aluminum metaphosphate [Al(PO$_3$)$_3$], aluminum orthophosphate [ALPO$_4$], and the amorphous, porous aluminum phosphates prepared and described as in U.S. Pat. No. 4,845,069, which is incorporated herein by reference. In an alternative form, the catalyst can comprise phosphorus pentoxide, phosphoric acid or any other phosphate ion source, such as ammonium phosphate or an organophosphate ester wherein the ester moiety is susceptible to hydrolysis, mounted on alumina or silica-alumina. It is believed that this combination produces amorphous aluminum phosphate in situ. The mounted catalyst can be prepared by depositing the source of phosphate ion on alumina or silica-alumina, typically, in a molar ratio ranging from about 0.01 mole to about 1 mole phosphorus per mole aluminum. The phosphate-treated support is then calcined at a temperature between about 200° C. and about 800° C. to drive off water or to convert the source of phosphate into the phosphate ion. Among the aforementioned catalysts, the preferred aluminum phosphate is aluminum orthophosphate [ALPO$_4$].

Alternatively, the catalyst can be any aluminophosphate molecular sieve, which is typically characterized as having a crystalline framework structure whose chemical composition expressed in terms of mole ratios of oxides is:

$Al_2O_3: 1.0 \pm 0.2\ P_2O_5$

Each framework structure is microporous, and the pores are essentially uniform having nominal diameters within the range of from about 3 to about 12 angstrom units. Suitable, non-limiting examples of aluminophosphate molecular sieves, designated ALPO's, include ALPO-5, ALPO-8, ALPO-9, ALPO-11, ALPO-12, ALPO-14, ALPO-16, ALPO-17, ALPO-18, ALPO-20, ALPO-21, ALPO-22, ALPO-23, ALPO-25, ALPO-26, ALPO-28, ALPO-31, and ALPO-33, as well as, VPI-5. Detailed descriptions of the aforementioned aluminophosphate molecular sieves and the preparations thereof can be found in *Molecular Sieves,* by R. Szostak, Van Nostrand Rinehold Publishers, 1988, relevant sections of which are incorporated herein by reference.

As a variation of the above, the catalyst employed in the process of this invention can be any silicoaluminophosphate molecular sieve. The silicoaluminophosphate molecular sieves are also microporous crystalline materials, the pores again being essentially uniform and have nominal diameters of from about 3 to about 12 Angstroms. The crystalline structure of the silicoaluminophosphate molecular sieves comprises an aluminophosphate framework structure which is further substituted with silicon. Silicoaluminophosphates, designated SAPO's, which are suitable for the process of this invention include, but are not limited to, SAPO-5, SAPO-11, SAPO-16, SAPO-17, SAPO-20, SAPO-31, SAPO-35, SAPO-37, SAPO-40, SAPO-41, SAPO-42, and SAPO-44, as well as silicon-substituted VPI-5. Detailed descriptions of the aforementioned silicoaluminophosphate molecular sieves and their preparations can be found in *Molecular Sieves,* by R. Szostak, op. cit., the relevant sections of which are incorporated herein by reference.

Any weight ratio of cyclopentenol or substituted cyclopentenol to catalyst is suitable for the process of this invention provided that the ratio is capable of producing the desired cyclopentadiene product. Generally, the weight ratio of cyclopentenol or substituted cyclopentenol to catalyst varies between about 5:1 and about 100:1. Preferably, the weight ratio of cyclopentenol to catalyst varies between about 10:1 and 50:1.

The process of this invention can be conducted in any suitable reactor, such as, fixed bed reactors, continuous flow reactors, distillation reactors, fluid bed reactors, and transport reactors. Preferred is a distillation reactor wherein an azeotropic mixture comprising the cyclopentadiene product and a by-product of water is continuously distilled from the reaction process, thereby driving the reaction to completion. Another preferred reactor design is a fixed-bed continuous flow reactor.

The cyclopentenol or substituted cyclopentenol can be introduced into the reactor as a neat liquid or as a vapor, but preferably, as a neat liquid. Optionally, if the cyclopentenol is solid, it can be dissolved in a suitable solvent and introduced into the reactor as a solution. Suitable solvents are nonreactive in the process of the invention, are liquid under the process conditions, and are capable of dissolving the cyclopentenol. Examples of inert solvents include toluene, xylenes, and mesitylene.

Any operable process conditions can be employed which produce the desired cyclopentadiene or substituted cyclopentadiene product. Typically, the reaction temperature varies between about 50° C. and about 200° C, preferably, between about 100° C. and about 150° C. Below about 50° C. the process may be slow, or the cyclopentenol may be a solid and difficult to handle. Above about 200° C. the selectivity to the cyclopentadiene may be low. The pressure can vary from subatmospheric to superatmospheric, but typically ranges from about 0.005 atm to about 4 atm. In a batch reactor the pressure is autogenous. For complete conversion the residence time of the cyclopentenol in a batch reactor commonly varies from only about 1 to about 2 hours. In a flow reactor the residence time of the cyclopentenol and the relative amounts of cyclopentenol to catalyst are determined by the liquid hourly space velocity (LHSV), defined as the grams of liquid feed per gram catalyst per hour, or simply hr-$^1$. Typically, the liquid hourly space velocity ranges from about 0.1 hr-$^1$ to about 100 hr-$^1$. If the cyclopentenol is functionalized with an air-sensitive moiety, such as an amine, then air can be excluded from the reactor and replaced with an inert gaseous diluent, such as nitrogen, argon, or helium.

When cyclopentenol or a substituted cyclopentenol is contacted with any of the aforementioned catalysts in the manner described hereinabove, cyclopentadiene or a substituted cyclopentadiene is produced. Preferred cyclopentadiene products may be represented by the formula:

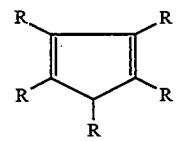

wherein each R is independently selected as defined previously in connection with the cyclopentenol reagent. Preferably, each R is independently hydrogen or a $C_{1-10}$ hydrocarbyl moiety, more preferably, hydrogen or a $C_{1-6}$ hydrocarbyl moiety, most preferably hydrogen or methyl.

Other preferred products can be represented by the formulas:

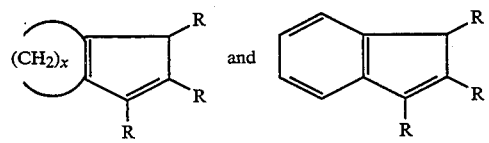

as well as the formula:

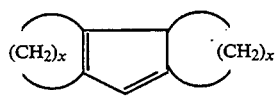

and the formula:

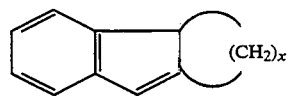

wherein R is as defined hereinbefore, and x is an integer from 3 to 6, preferably 4.

Non-limiting examples of the above-identified cyclopentadiene products include unsubstituted cyclopentadiene, tetramethylcyclopentadiene, dimethylcyclopentadiene, ethylcyclopentadiene, acetoxycyclopentadiene, methoxycyclopentadiene, phenylcyclopentadiene, indene, tetrahydroindene, benzyltetramethylcyclopentadiene, phenyltetramethylcyclopentadiene, ethyltetramethylcyclopentadiene, pentamethylcyclopentadiene, 1,3-di-t-butylcyclopentadiene, 1,2,3,4-tetrahydrofluorene, and 1,2,3,4,5,6,7,8-octahydrofluorene. Preferably, four R groups are methyl; one R group is hydrogen, and the product is tetramethylcyclopentadiene. In a second preferred embodiment, all five R groups are methyl, and the product is pentamethylcyclopentadiene. In third and fourth preferred embodiments, two adjacent R moieties together form a saturated or unsaturated $C_4$ hydrocarbyl moiety, and the products are tetrahydroindene and indene, respectively.

The separation of the cyclopentadiene product from the heterogeneous catalyst of this invention is straightforward. The catalyst is simply filtered from the product stream. Water is removed from the product stream by distillation or separatory filtration. The cyclopentadiene or substituted cyclopentadiene product can be used as is or further purified by methods known in the art.

The isolated yields of cyclopentadiene and substituted cyclopentadienes derived from the process of this invention are generally high. Typically, the yield of cyclopentadiene or substituted cyclopentadiene is at least about 75 mole percent, preferably, at least about 80 mole percent based on the moles of cyclopentenol reactant.

The following examples are presented to illustrate the process and claims of this invention, but should not be construed to be limiting of the scope thereof.

EXAMPLE 1

(a) Following the general hydrogenation procedure outlined in *Organometallics*, 6, No. 9, 1987, pages 1947–1954, 2,3,4,5-tetramethylcyclo-2-penten-1-one is reduced to 2,3,4,5-tetramethylcyclo-2-penten-1-ol. To a slurry of 2,3,4,5-tetramethylcyclo-2-penten-1-one (Aldrich Chemical Company, Inc., 49.3 g, 0.357 mol) in 300 ml of diethyl ether cooled to 0° C. is slowly added lithium aluminum hydride (12.6 g; 0.337 mol). The resulting slurry is warmed to 25° C. and stirred for 2 hr. Another portion of lithium aluminum hydride (7.7 g, 0.20 mol) is then added, and the mixture is gently heated to reflux for 2 hr. The reaction is then sequentially quenched with water (20 mL), 20 mL of 15 percent aqueous sodium hydroxide, and 60 mL of water. After filtration, the ether layer is washed with water and dried over magnesium sulfate to yield 2,3,4,5-tetramethylcyclo-2-penten-1-ol.

(b) To a 25 ml one-neck round bottom flask are added 2,3,4,5-tetramethylcyclo-2-penten-1-ol (10.0 g, 71.3 mmol) and aluminum phosphate ($ALPO_4$, 0.60 g, 4.92 mmol). The contents of the flask are heated under partial vacuum (5–10 mm Hg) to distill over 1,2,3,4-tetramethylcyclopentadiene and water. The water is removed by pipette, with the last traces being removed by drying over anhydrous magnesium sulfate to give 1,2,3,4-tetramethylcyclopentadiene (7.5 g, 85 mole percent isolated yield).

EXAMPLE 2

2,3,4,5-Tetramethylcyclo-2-penten-1-ol is dehydrated to tetramethylcyclopentadiene according to the procedure of Example 1(b), with the exception that ALPO-8 (0.500 g) is used as the catalyst instead of aluminum phosphate. The isolated yield of tetramethylcyclopentadiene is 7.25 g (82 mole percent).

EXAMPLE 3

2,3,4,5-Tetramethylcyclo-2-penten-1-ol is dehydrated to tetramethylcyclopentadiene according to the procedure of Example 1(b), with the exception that SAPO-5 (0.500 g) is used as the catalyst instead of aluminum phosphate. The isolated yield of tetramethylcyclopentadiene is 7.3 g (83 mole percent).

EXAMPLE 4

2,3,4,5-Tetramethylcyclo-2-penten-1-ol is dehydrated to tetramethylcyclopentadiene according to the procedure of Example 1(b), with the exception that SAPO-11 (0.50 g) is used as the catalyst instead of aluminum phosphate. The yield of tetramethylcyclopentadiene is 7.0 g (79 mole percent).

EXAMPLE 5

2,3,4,5-Tetramethylcyclo-2-penten-1-ol is dehydrated to tetramethylcyclopentadiene according to the procedure of Example 1(b), with the exception that SAPO-5 (0.250 g) is used as the catalyst instead of aluminum phosphate. The yield of tetramethylcyclopentadiene is 6.6 g (76 mole percent).

EXAMPLE 6

To a 25 ml one-neck round bottom flask are added 1-indanol (10 g, 75 mmol) and aluminum phosphate ($ALPO_4$, 1.0 g, 8.2 mmol). The contents of the flask are heated under partial vacuum (5–10 mm Hg) to distill over indene and water. The water is removed by pipette, with the last traces being removed by drying over anhydrous magnesium sulfate to give indene (8 g) in an isolated yield of 92 mole percent.

What is claimed is:

1. A process of preparing cyclopentadiene or substituted cyclopentadiene comprising contacting cyclopentenol or a substituted cyclopentenol with a catalytic amount of a catalyst selected from the group consisting of aluminophosphate molecular sieves and silicoaluminophosphate molecular sieves, the contacting being conducted under reaction conditions sufficient to form cyclopentadiene or a substituted cyclopentadiene.

2. The process of claim 1 wherein the cyclopentenol is represented by the following isomeric formulas:

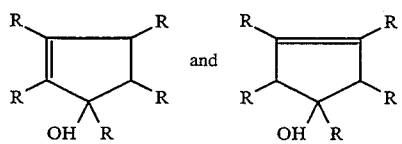

wherein each R is independently hydrogen, a $C_{1-10}$ hydrocarbyl moiety, or wherein up to two R moieties are each independently a halogen, ketone, amine, ether, carboxylic acid, or ester moiety.

3. The process of claim 2 wherein the cyclopentenol is 2,3,4,5-tetramethylcyclo-2-penten-1-ol or 2,3,4,5-tetramethylcyclo-3-penten-1-ol.

4. The process of claim 1 wherein the cyclopentenol is selected from the group consisting of the formulas:

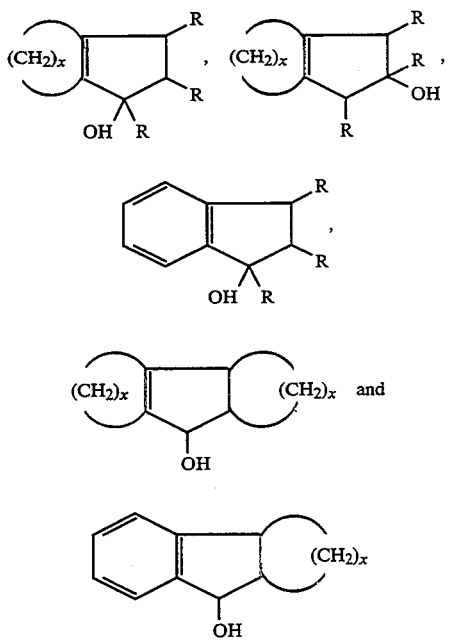

wherein each R is independently hydrogen or a $C_{1-10}$ hydrocarbyl moiety and x is an integer from 3 to 6.

5. The process of claim 4 wherein the cyclopentenol is selected from the group consisting of 1-indanol, 4,5,6,7-tetrahydro-1-indanol, and 4,5,6,7-tetrahydro-2-indanol.

6. The process of claim 1 wherein the catalyst is an aluminophosphate molecular sieve.

7. The process of claim 6 wherein the catalyst is AL-PO-8.

8. The process of claim 1 wherein the catalyst is a silicoaluminophosphate molecular sieve.

9. The process of claim 8 wherein the catalyst is SAPO-5.

10. The process of claim 8 wherein the catalyst is SAPO-11.

11. The process of claim 1 wherein the weight ratio of cyclopentenol or substituted cyclopentenol to catalyst varies from about 5:1 to about 100:1.

12. The process of claim 1 wherein the temperature ranges from about 50° C. to about 200° C. and wherein the pressure ranges from about 0.005 atm to about 4 atm.

13. The process of claim 1 wherein the process is conducted in a distillation reactor or a fixed bed, continuous flow reactor.

14. The process of claim 1 wherein the liquid hourly space velocity ranges from about 0.1 hr$^{-1}$ to about 100 hr$^{-1}$.

15. The process of claim 1 wherein the cyclopentadiene or substituted cyclopentadiene product is represented by the formula:

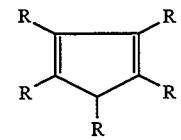

wherein each R is independently hydrogen, a $C_{1-10}$ hydrocarbyl moiety, or wherein up to two R moieties are each independently a halogen, ketone, amine, ether, carboxylic acid, or ester moiety.

16. The process of claim 15 wherein the product is tetramethylcyclopentadiene or pentamethylcyclopentadiene.

17. The process of claim 1 wherein the cyclopentadiene product is selected from the group consisting of the formulas:

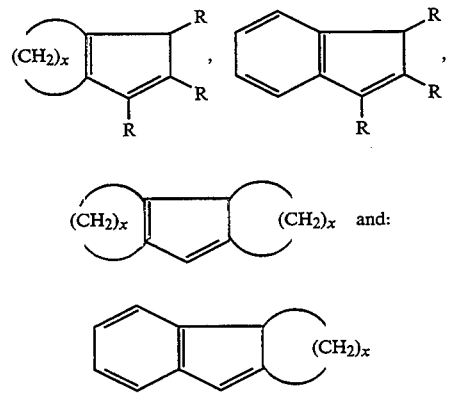

wherein each R is independently hydrogen or a $C_{1-10}$ hydrocarbyl moiety, and x is an integer from 3 to about 6.

18. The process of claim 1 wherein the product is indene or tetrahydroindene.

19. A process for preparing tetramethylcyclopentadiene comprising contacting 2,3,4,5-tetramethylcyclo-2-penten-1-ol or 2,3,4,5-tetramethylcyclo-3-penten-1-ol with a catalytic amount of a catalyst selected from the group consisting of aluminophosphate molecular sieves and silicoaluminophosphate molecular sieves, the contacting being conducted at a temperature between about 50° C. and about 200° C. under reaction conditions sufficient to form tetramethylcyclopentadiene.

20. The process of claim 19 wherein the isolated yield of tetramethylcyclopentadiene is at least about 80 mole percent, based on the moles of cyclopentenol reactant.

* * * * *